United States Patent [19]
Arhancet et al.

[11] Patent Number: 5,945,570
[45] Date of Patent: Aug. 31, 1999

[54] CATALYST AND PROCESS FOR PREPARING 1,3-PROPANEDIOL

[76] Inventors: Juan Pedro Arhancet, 20667 Castle Bend Dr., Katy, Tex. 77450; Paul Himelfarb, 15802 Sandy Hill Dr., Houston, Tex. 77084; Joseph Broun Powell, 10506 Normont Dr., Houston, Tex. 77070; Robert Alfred Plundo, 6307 Paderborne Dr., Hudson, Ohio 44236; Mohammed Shahjahan Kazi, 9948 Patton St., Twinsburg, Ohio 44087; William Joseph Carrick, 11500 Boxwood Cir., Chardon, Ohio 44024

[21] Appl. No.: 09/182,380

[22] Filed: Oct. 29, 1998

[51] Int. Cl.$^6$ ........................................ C07C 29/14
[52] U.S. Cl. ................... 568/862; 568/852; 568/867
[58] Field of Search ........................ 568/852, 862, 568/867

[56] References Cited

U.S. PATENT DOCUMENTS

| | | |
|---|---|---|
| 2,419,300 | 4/1947 | Tollefson . |
| 2,434,110 | 1/1948 | Hatch . |
| 2,879,307 | 3/1959 | Von Bezard . |
| 3,687,981 | 8/1972 | Lawrence et al. .................. 260/340.7 |
| 3,808,280 | 4/1974 | Merger . |
| 3,850,744 | 11/1974 | Plundo et al. ........................... 208/210 |
| 3,876,532 | 4/1975 | Plundo et al. ........................... 208/216 |
| 4,181,810 | 1/1980 | Immel ..................................... 568/807 |
| 5,093,537 | 3/1992 | Unruh et al. ............................ 568/862 |
| 5,256,827 | 10/1993 | Slaugh et al. .......................... 568/454 |
| 5,304,691 | 4/1994 | Arhancet ................................ 568/867 |
| 5,334,778 | 8/1994 | Haas ....................................... 568/862 |
| 5,344,993 | 9/1994 | Slaugh et al. .......................... 568/454 |
| 5,449,653 | 9/1995 | Briggs et al. ........................... 502/166 |
| 5,463,145 | 10/1995 | Powell et al. .......................... 568/867 |
| 5,786,524 | 7/1998 | Powell et al. .......................... 568/862 |

*Primary Examiner*—Gary Geist
*Assistant Examiner*—Jean F Vollano

[57] ABSTRACT

A solid, particulate catalyst composition is provided containing an active nickel component in which the nickel constitutes from about 25 to about 60 wt % of the catalyst composition; a molybdenum component in which the molybdenum constitutes from about 5 to about 20 wt % of the catalyst composition; and a binder component comprising at least one of oxides of silica, zirconium, aluminum, zinc and calcium, each of the calcium, aluminum and zinc being present in an amount no greater than about 2 wt %, preferably about 0 to 1 wt %. The catalyst is designed for the selective hydrogenation of 3-hydroxypropanal to 1,3-propanediol in aqueous solution.

8 Claims, 2 Drawing Sheets

CATALYST AND PROCESS FOR PREPARING 1,3-PROPANEDIOL

BACKGROUND OF THE INVENTION

This invention relates to the manufacture of 1,3-propanediol. In one aspect, the invention relates to an improved catalyst for hydrogenating 3-hydroxypropanal to 1,3-propanediol which exhibits prolonged catalyst life in the hydrogenation reaction environment. In a further aspect, the invention relates to an improved process for preparing 1,3-propanediol from 3-hydroxypropanal.

1,3-propanediol, a chemical intermediate in the preparation of polyesters, can be prepared by hydrogenation of 3-hydroxypropanal in aqueous solution. Selective hydrogenation of 3-hydroxypropanal to 1,3-propanediol is complicated by the high reactivity of 3-hydroxypropanal and the relatively low solubility of hydrogen in aqueous solution.

Hydrogenation in a trickle-bed configuration is favored by small catalyst particle size. However, catalyst crush strength is significantly diminished with reduced catalyst particle size. A common approach to increasing the crush strength of nickel-based bulk catalysts is to increase the amount of calcium in the binder. However, in the aqueous hydrogenation environment, calcium and other soluble binder components are quickly leached from the catalyst. This has two negative effects on the synthesis process. First, as the water is evaporatively separated from the 1,3-propanediol, the leached binder material is deposited in the evaporation column, resulting in down-time and equipment clean-up costs. Second, the removal of these soluble components from the particulate catalyst lowers the crush strength of the catalyst, resulting in less efficient flow-through in the catalyst bed as areas of catalyst collapse and eventually plug the bed.

It is therefore an object of the invention to provide a catalyst and process particularly designed for the hydrogenation of 3-hydroxypropanal to 1,3-propanediol in aqueous solution. In one embodiment, it is an object of the invention to provide a catalyst for the hydrogenation of 3-hydroxypropanal having reduced leachable content without significant reduction of crush strength in the reaction environment.

SUMMARY OF THE INVENTION

According to the invention, a solid catalyst composition is provided containing an active nickel component in which the nickel constitutes from about 25 to about 60 wt % of the catalyst composition; a molybdenum component in which the molybdenum constitutes from about 5 to about 20 wt % of the catalyst composition; and a binder component comprising from about 10 to about 50 wt % of a binder material selected from at least one of oxides of silicon and silicates and oxides of zirconium, aluminum, zinc and calcium, with the aluminum, calcium and zinc each present in the catalyst composition in an amount no greater than 2 wt %, preferably 0–1 wt %.

Further according to the invention, a process for preparing 1,3-propanediol is provided comprising contacting an aqueous solution of 3-hydroxypropanal under hydrogenation conditions with a catalyst containing an active nickel component in which the nickel constitutes from about 25 to about 60 wt % of the catalyst composition; a molybdenum component in which the molybdenum constitutes from about 5 to about 20 wt % of the catalyst composition; and a binder component comprising from about 10 to about 50 wt % of a binder material selected from at least one of silicates and oxides of zirconium, aluminum, zinc and calcium, with the aluminum, calcium and zinc each present in the catalyst composition in an amount no greater than 2 wt %, preferably 0–1 wt %.

The use of the described catalyst in the hydrogenation of aqueous 3-hydroxypropanal permits the production of 1,3-propanediol in high yields with reduced downtime from the effects of the use of soluble binder materials.

DETAILED DESCRIPTION OF THE INVENTION

Figure 1:
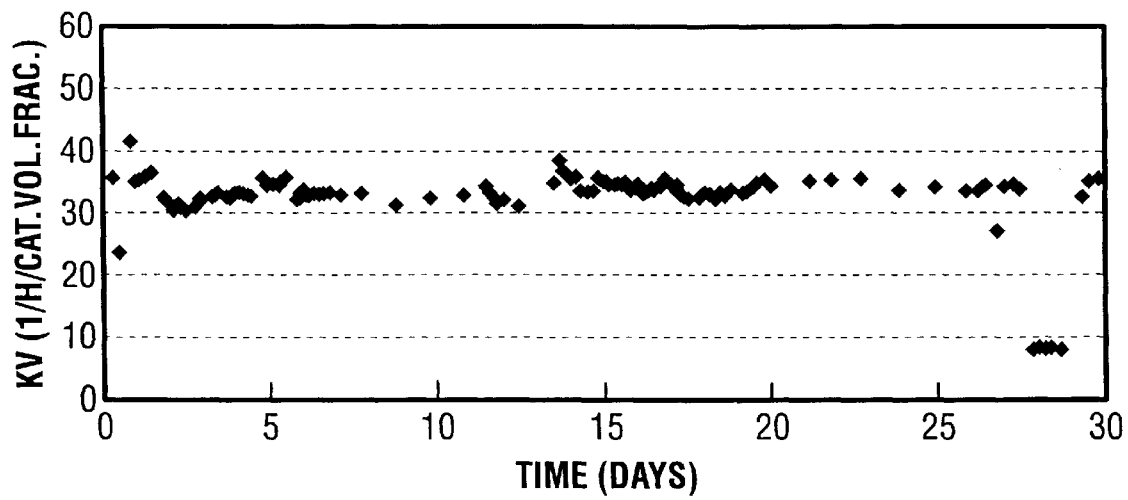
FIG. 1 is a plot of catalyst activity over time for a 3-hydroxypropanal hydrogenation catalyst according to the invention.

The hydrogenation catalyst contains, as the major active component, from about 25 to about 60 wt % nickel (as $Ni^o$), preferably from about 30 to about 45 wt %. The nickel in the active catalyst is predominantly in reduced form.

The catalyst contains about 5 to about 20 wt % molybdenum (as $Mo^o$), preferably about 6 to about 16 wt %. The molybdenum is present in the catalyst in both metal and oxide form. The molybdenum has a binding function and is also an activity promoter.

The binder portion of the catalyst acts as a "glue" to hold the separate components together and to provide crush resistance from the pressure drop across the catalyst bed. The binder constitutes about 30 to about 70 wt % of the catalyst and is made up of oxides of silicon, and silicates and oxides of zinc, zirconium, calcium, magnesium and/or aluminum. Typically, the catalyst will contain from about 30 to about 70, preferably about 35 to about 55, wt % silicon; from about 0 to about 2, preferably about 0 to about 1, wt % zinc; and from about 0 to about 2 wt % aluminum. The binder will contain not more than about 2 wt % calcium, and will preferably contain 0–1 wt % calcium. A preferred embodiment of the catalyst contains essentially no zinc or calcium. The preferred catalyst composition for hydrogenation of 3-hydroxypropanal to 1,3-propanediol in aqueous solution contains about 35 wt % nickel and about 8–12 wt % molybdenum, with the balance binder material as described above.

The catalyst can be prepared by any procedure that incorporates the active nickel component, the molybdenum component and the binder material in a solid bulk form. In general, catalyst preparation involves mixing nickel oxide, the binder material such as attapulgus clay, and molybdenum trioxide powder into a homogeneous powder. Next, a solution of colloidal silica in sufficient water to form an extrudable mixture is stirred into the solid mixture. The wet mixture is then extruded through a die plate with 0.040–0.070" diameter holes. The extrudates are dried at 100–125° C. for a time sufficient to reduce the moisture content to less than about 5 wt %. The dried extrudates are then calcined in air at 450–550° C. for at least about 3 hours until the desired strength is developed. Prior to use, the catalyst is reduced under hydrogen gas at a temperature within the range of about 350 to about 450° C. for a time sufficient for reduction of at least about 60% of the nickel. If the reduced catalyst is not used immediately, it is cooled to ambient and stored under a protective medium such as 1,3-propanediol until used. Illustrative catalyst preparations are provided in Examples 2 and 3.

The catalyst is in particulate form, with particle size and shape such as to provide sufficient catalyst activity dependent upon other process variables such as flow rate and pressure. The preferred catalyst particles are less than 1/8" in diameter (across the width of the particle cross-section), preferably about 1/16–1/32", to provide an optimum balance of geometric surface area and crush resistance. The preferred catalyst shapes for longest catalyst bed life are trilobal and cylindrical.

The catalyst will preferably exhibit an activity of at least about 10 $h^{-1}$/catalyst volume fraction, preferably at least about 20, in the selective hydrogenation of 3-hydroxypropanal to 1,3-propanediol. The catalyst has improved stability in the reaction environment and good physical integrity over the catalyst active life.

Hydrogenation of the 3-hydroxypropanal to 1,3-propanediol can be carried out in aqueous solution at an temperature of at least about 30° C., generally within the range of about 50 to about 175° C., under a positive hydrogen pressure of at least about 100 psig, generally within the range of about 200 to about 2000 psig. Hydrogenation of HPA to PDO is disclosed in U.S. Pat. No. 5,786,524, the disclosure of which is hereby incorporated by reference.

The invention hydrogenation process is designed particularly for use in a process for preparing 1,3-propanediol by the hydroformylation of ethylene oxide, as described for example in U.S. Pat. Nos. 5,463,145 and 3,687,981, or from acrolein, as described in U.S. Pat. No. 5,093,537, the disclosures of which are hereby incorporated by reference.

In such processes, 3-hydroxypropanal is an intermediate product which is hydrogenated in aqueous solution to 1,3-propanediol. In one such process, ethylene oxide is hydroformylated (reacted with carbon monoxide and hydrogen) at a temperature within the range of about 50 to about 140° C. and a $CO/H_2$ pressure within the range of about 500 to about 5000 psig, preferably about 60 to about 90° C. and about 1000 to about 3500 psig, in the presence of a suitable hydroformylation catalyst such as cobalt or rhodium carbonyl to produce a hydroformylation product mixture containing 3-hydroxypropanal, 1,3-propanediol and hydroformylation reaction by-products. The 3-hydroxypropanal component is removed by extraction into water and passed to a hydrogenation reaction vessel in the form of an aqueous solution having a 3-hydroxypropanal concentration less than 15 wt %, preferably less than about 10 wt %, based on the weight of the aqueous solution. The hydrogenation of 3-hydroxypropanal to 1,3-propanediol is carried out as described above to form a hydrogenation product mixture containing 1,3-propanediol as the major product, which is recovered by suitable means such as distillation.

EXAMPLE 1

Conventional 1,3-Propanediol Catalyst Preparation. In a typical batch catalyst preparation, a precipitation tank is loaded with 2200 parts of nickel chloride solution (97–98% $NiCl_2$), 70 parts of Microcel E (0.8 solids), and 130 parts of alumina from sodium aluminate solution. After the precipitation is complete, the liquid is poured off and the solids are washed with deionized water several times. The solid mass (nickel calcium silicate) is dried and calcined in air at 390–410° C.

A one-gallon plow-type mixer is charged with 730 parts of technical grade nickel calcium silicate (93–97% $NiCaSiAlO_x$), 125 parts of Microcel E (0.8 solids) and 125 parts bentonite clay (0.8 solids) and mixed for 2 minutes. Next, a solution containing 600 parts of deionized water and 16–20 parts of molybdenum from ammonium molybdate solution is stirred into the mixture, and mixing is continued for 5–10 minutes. The wet mix is then extruded through a die plate with 0.06" to 0.07" diameter holes of trilobe form. The extrusions are dried overnight at 100–125° C. The dried intermediate is then reduced with hydrogen at 445–455° C. to a reduced nickel content of about 90%, based on total nickel.

EXAMPLE 2

Invention Catalyst Preparation. A one-gallon plow-type mixer was charged with 750 parts of technical-grade nickel oxide (93–97% NiO), 498 parts of Attagel-30 attapulgus clay (0.8 solids), and 185 parts of molybdenum trioxide powder ($MoO_3$) and mixed for 2–3 minutes. A solution of 796 parts Nalco 2327, a colloidal silica sol (available from Nalco Chemical Company), in 200 parts deionized water was added to the dry blend with stirring. Stirring was continued for 5 minutes. About 60 parts of additional deionized water was added to the mixer and stirring was continued for another 5 minutes. The wet mix was then extruded through a single celcon tri-insert which contained holes 0.040 inch in diameter. The extrudates were dried at 110° C., then sized/screened and calcined in air at 500° C. for about 3 hours in a stationary ceramic sagger. The extrudates were then reduced with hydrogen at 420–430° C. to an RVR level of 0.9.

EXAMPLE 3

Invention Catalyst Preparation. A one-gallon plow-type mixer was charged with 735 parts of technical-grade nickel oxide (93–97% NiO), 355 parts Attagel 30 attapulgus clay (0.8 solids) and 286 parts of molybdenum trioxide powder ($MoO_3$) and mixed for 2 minutes. A solution of 795 parts of Nalco 2327 colloidal silica in 225 parts deionized water was added to the solid mixture with stirring, and the stirring was continued for 10 minutes. The wet mix was then extruded through a die plate with 0.040–0.070" diameter holes. The extrudates were dried overnight at 100–125° C. The dried intermediate was then calcined in air at 500° C. for about 3 hours and subsequently hydrogen reduced at 420–430° C. to an RVR of 0.9.

EXAMPLE 4

Hydrogenation of 3-Hydroxypropanal. Four hydrogenation catalyst runs (catalysts A, B, C, D, from Table 1) were performed in a 1.2" diameter trickle-bed reactor. The reactor was loaded with 400 mL of the selected hydrogenation catalyst. The reactor was pressurized to 1500 psig with hydrogen, and a stream of deionized, degassed water was continuously fed into the reactor. Part of the stream exiting the reactor was continuously returned to the inlet and mixed with the incoming feed so that the superficial liquid velocity (mL/s liquid coming into the reactor divided by $cm^2$ cross section area of reactor) in the reactor was between 0.3 and 0.8 cm/s. When the desired temperature of 60° C. was reached in the reactor, the water feed was discontinued and an aqueous stream containing about 30%

3-hydroxypropanal was fed in. The heat of reaction was removed by heat exchange in the recirculation loop. Pressure was maintained by continuous addition of hydrogen to replace consumed gas. Samples of feed and product were periodically taken and the concentration of 3-hydroxypropanal was determined. Assuming a first-order reaction rate with respect to 3-hydroxypropanal concentration, an apparent reaction rate constant was calculated for each feed/product pair of 3-hydroxypropanal concentrations. The activity of the catalyst to hydrogenate 3-hydroxypropanal was calculated as the reaction rate constant, expressed in units of "volume of liquid/volume of catalyst particles/time."

The reaction rates of catalysts A to D were measured over a period of about 30 days. Catalyst C is a standard, off-the-shelf nickel hydrogenation catalyst containing a relatively low molybdenum content (1.8 wt %). Catalysts A, B and D are invention catalysts designed for more stable hydrogenation of 3-hydroxypropanal in aqueous solution. Results are shown in Figures A to E and in Table 1.

Since the reaction rate is limited primarily by the diffusion rate of reactants inside the catalyst particles, smaller extrudate cross-sections give more favorable reaction rate constants. Crush strength of the catalyst particles decreases with decreasing extrudate cross section dimension. Catalyst C was too weak to be extruded using 1/32" holes and was therefore extruded using 1/16" holes. Calcium, when present in the catalyst, was leached almost completely within a short period of time, causing fouling of the heat exchanger used for evaporation of water in a subsequent 1,3-propanediol concentration step.

(ii) a molybdenum component in which the molybdenum constitutes from about 5 to about 20 wt % of the catalyst composition; and (iii) from about 10 to about 50 wt %, based on the weight of the catalyst composition, of a binder material comprising at least one of oxides of silicon and silicates and oxides of zinc, aluminum, zirconium and calcium, each of said aluminum, calcium and zinc present in an amount no greater than about 2 wt %, based on the weight of the catalyst composition, to produce an aqueous product mixture comprising 1,3-propanediol; and (b) recovering the 1,3-propanediol from the aqueous product mixture.

2. The process of claim 1 in which the molybdenum constitutes from about 6 to about 16 wt % of the catalyst composition.

3. The process of claim 1 in which the solid particles are about 1/16" in diameter.

4. The process of claim 1 in which the solid particles are about 1/32" in diameter and cylindrical in shape.

5. The process of claim 1 in which, in the catalyst composition, each of zinc and calcium is present in an amount not greater than about 1 wt %, based on the weight of the catalyst composition.

6. The process of claim 1 in which 3-hydroxypropanal is present in the aqueous reaction mixture in an amount less than 15 wt %.

7. The process of claim 1 in which the 1,3-propanediol is recovered from the aqueous product mixture by evaporative distillation.

TABLE 1

| | A 1/32" cylinder | | B 1/32" cylinder | | C 1/16" trilobe | | D 1/16" trilobe | |
|---|---|---|---|---|---|---|---|---|
| | fresh | after 38 days | fresh | after 28 days | fresh | after 21 days | fresh | after 28 days |
| Ni | 35.3 | 37.0 | 35.5 | not | 56.9 | 56.9 | 36.0 | not |
| Si | 16.2 | 15.9 | 14.2 | available | 4.7 | 6.2 | 15.7 | available |
| Al | 1.5 | 1.6 | 0.9 | | 3.5 | 5.2 | 1.3 | |
| Mo | 7.8 | 8.0 | 12.0 | | 1.8 | 1.6 | 8 | |
| Ca | 0.8 | 0.1 | 0.7 | | 4.6 | 0.2 | 0.9 | |
| Zn | 0 | 0 | 0 | | 0.0 | 0.0 | 0 | |
| Fe | 0.6 | 0.5 | 0.4 | | 0.5 | 0.6 | 0.5 | |
| Na | 0.0 | 0 | 0 | | 0.2 | 0.2 | 0 | |
| La | 0.4 | 0.1 | 0.1 | | 0 | 0 | 0.1 | |
| Crush Strength lb/mm | 2.3 | 1.3 | 3.4 | 1.7 | 1.7 0.9 (1/32) | 1.3 after 45 days | 5.2 | 3.1 |
| Average Activity | 35[1] | | 25[2] | | 25[3] | | 30[4] | |

Figure 2:
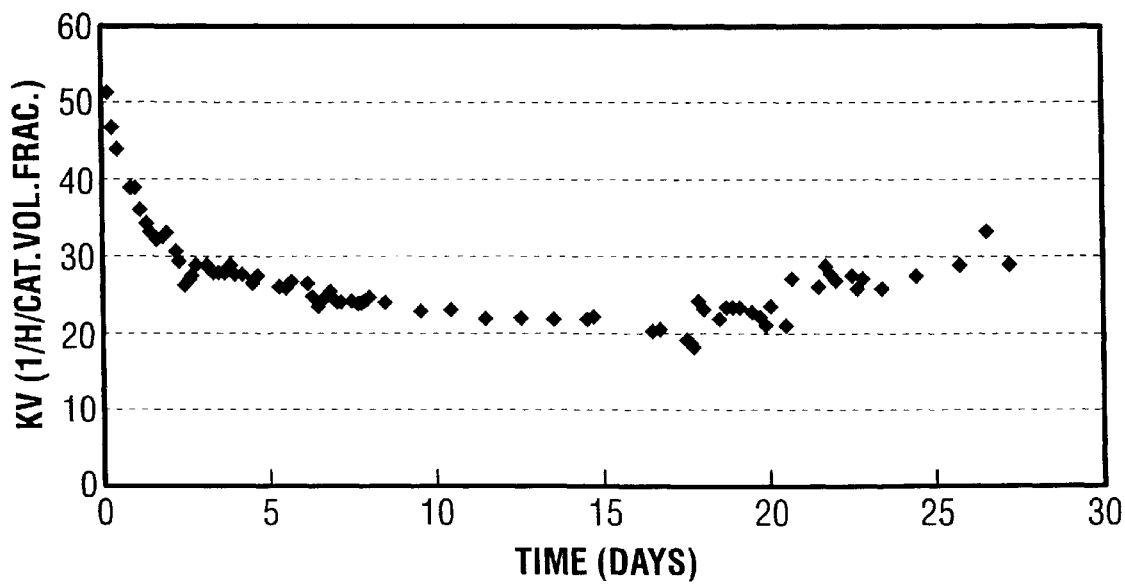
FIG. 2 is a plot of catalyst activity over time for a 3-hydroxypropanal hydrogenation catalyst according to the invention.
Figure 3:
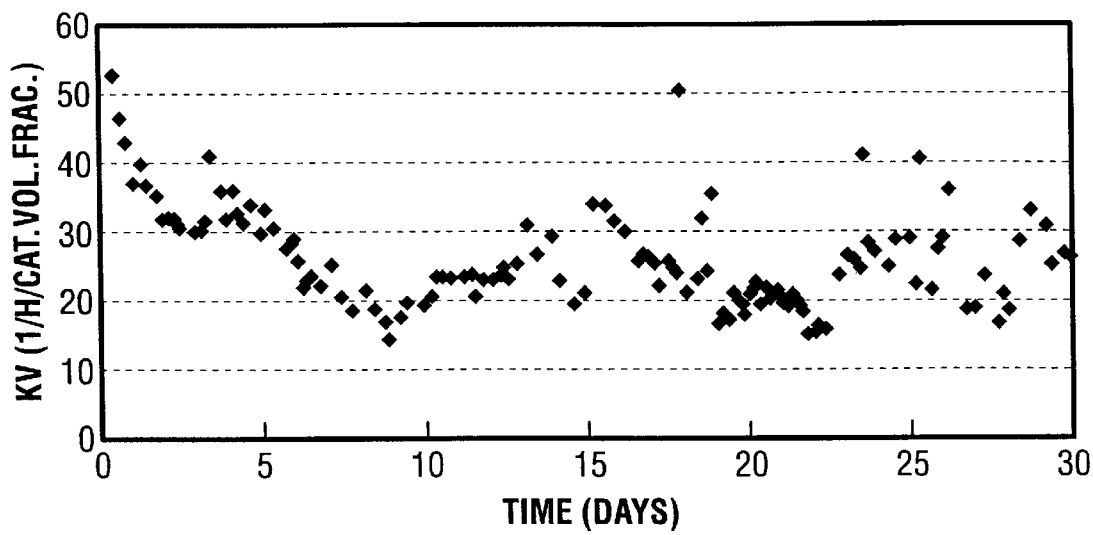
FIG. 3 is a plot of catalyst activity over time for a conventional nickel hydrogen catalyst.
Figure 4:
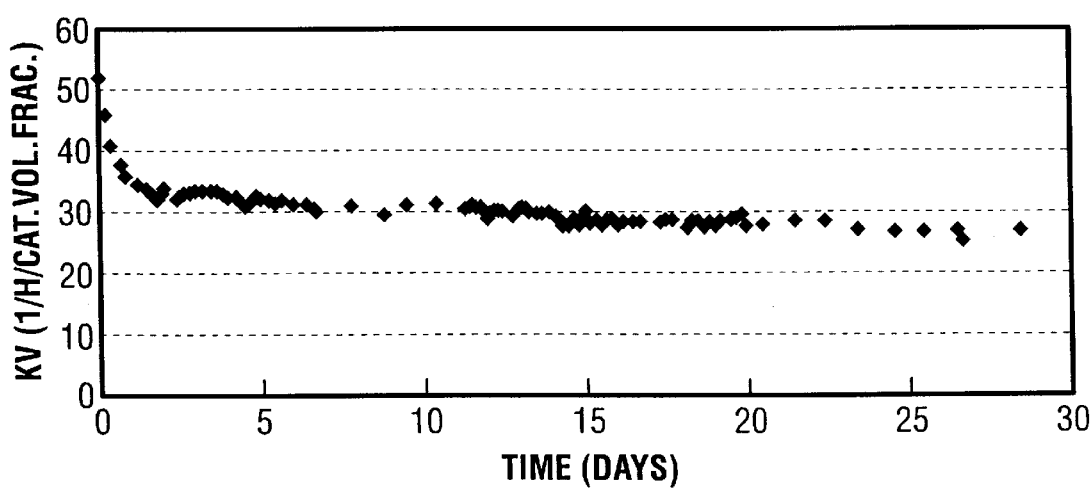
FIG. 4 is a plot of catalyst activity over time for a 3-hydroxypropanal hydrogen catalyst according to the invention.

[1]See FIG. 1.
[2]See FIG. 2.
[3]See FIG. 3.
[4]See FIG. 4.

We claim:

1. A process for preparing 1,3-propanediol from 3-hydroxypropanal comprising:

(a) contacting, in an aqueous reaction mixture at a temperature within the range of about 30 to about 175° C., 3-hydroxypropanal and hydrogen in the presence of a solid particulate catalyst composition comprising
(i) an active nickel component in which the nickel constitutes from about 25 to about 60 wt % of the catalyst composition;

8. A process for preparing 1,3-propanediol comprising the steps of:

(a) contacting ethylene oxide with carbon monoxide and hydrogen under hydroformylation conditions and in the presence of an effective amount of a hydroformylation catalyst, to form a reaction product mixture comprising 3-hydroxypropanal;

(b) removing 3-hydroxypropanal from the reaction product mixture and forming an aqueous solution thereof;

(c) adding to the aqueous solution of 3-hydroxypropanal a solid particulate hydrogenation catalyst composition comprising
  (i) an active nickel component in which the nickel constitutes from about 25 to about 60 wt % of the catalyst composition;
  (ii) a molybdenum component in which the molybdenum constitutes from about 5 to about 20 wt % of the catalyst composition; and
  (iii) from about 10 to about 50 wt %, based on the weight of the catalyst composition, of a binder material comprising at least one of silicates and oxides of zinc, aluminum, zirconium and calcium, each of said aluminum, calcium and zinc present in an amount no greater than about 2 wt %, based on the weight of the catalyst composition.

(d) heating the aqueous solution of 3-hydroxypropanal to a temperature within the range of about 30 to about 175° C. under a positive hydrogen pressure of at least about 100 psig, to produce a hydrogenation product mixture comprising 1,3-propanediol; and (e) recovering the 1,3-propanediol from the hydrogenation product mixture.

* * * * *